(12) United States Patent
Dal Molin

(10) Patent No.: US 7,711,422 B2
(45) Date of Patent: May 4, 2010

(54) ADJUSTING THE MAXIMUM VENTRICULAR STIMULATION FREQUENCY ACCORDING TO THE HEMODYNAMIC STATE OF THE PATIENT IN AN ACTIVE IMPLANTABLE MEDICAL DEVICE

(75) Inventor: Renzo Dal Molin, Chatillon (FR)

(73) Assignee: ELA Medical S.A.S., Montrouge (FR)

( * ) Notice: Subject to any disclaimer, the term of this patent is extended or adjusted under 35 U.S.C. 154(b) by 345 days.

(21) Appl. No.: 10/965,689

(22) Filed: Oct. 14, 2004

(65) Prior Publication Data

US 2005/0137635 A1    Jun. 23, 2005

(30) Foreign Application Priority Data

Oct. 16, 2003  (FR)  ................... 03 12106

(51) Int. Cl.
*A61N 1/365* (2006.01)
(52) U.S. Cl. ........................... 607/17; 600/508
(58) Field of Classification Search ............ 607/17–20, 607/24; 600/513, 547, 510, 526
See application file for complete search history.

(56) References Cited

U.S. PATENT DOCUMENTS

| | | | | |
|---|---|---|---|---|
| 3,897,789 A | | 8/1975 | Blanchard | 128/303.18 |
| 4,535,774 A | * | 8/1985 | Olson | 607/24 |
| 4,945,909 A | * | 8/1990 | Fearnot et al. | 607/14 |
| 5,085,215 A | * | 2/1992 | Nappholz et al. | 607/17 |
| 5,154,171 A | * | 10/1992 | Chirife | 607/24 |
| 5,156,147 A | * | 10/1992 | Warren et al. | 607/24 |
| 5,400,793 A | * | 3/1995 | Wesseling | 600/485 |
| 5,423,326 A | * | 6/1995 | Wang et al. | 600/526 |
| 5,500,006 A | * | 3/1996 | Heinze | 607/24 |
| 5,792,195 A | * | 8/1998 | Carlson et al. | 607/17 |
| 6,119,040 A | * | 9/2000 | Chirife | 607/18 |
| 6,408,209 B1 | | 6/2002 | Bouhour et al. | 607/19 |
| 6,473,644 B1 | | 10/2002 | Terry, Jr. et al. | 607/2 |
| 6,539,261 B2 | * | 3/2003 | Dal Molin | 607/20 |
| 6,556,866 B2 | * | 4/2003 | Dal Molin et al. | 607/9 |
| 6,604,002 B2 | * | 8/2003 | Molin | 607/28 |
| 6,725,091 B2 | * | 4/2004 | Dal Molin | 607/2 |
| 6,885,892 B1 | * | 4/2005 | Min et al. | 607/24 |
| 6,985,772 B2 | * | 1/2006 | Holmstrom et al. | 607/9 |
| 2001/0012953 A1 | * | 8/2001 | Molin et al. | 607/9 |
| 2001/0021864 A1 | * | 9/2001 | Molin | 607/17 |
| 2001/0031995 A1 | * | 10/2001 | Molin | 607/20 |
| 2001/0034540 A1 | * | 10/2001 | Molin | 607/20 |

\* cited by examiner

*Primary Examiner*—Carl H Layno
*Assistant Examiner*—Brian T Gedeon
(74) *Attorney, Agent, or Firm*—Orrick Herrington & Sutcliffe, LLP

(57) ABSTRACT

Adjusting the maximum ventricular stimulation frequency according to the hemodynamic state of the patient in an active implantable medical device. This device provides for limiting ventricular stimulation to a maximum frequency ($F_{max}$), the rate of delivery of the stimulation pulses, measuring an intracardiac bio-impedance ($Z_n$, $Z_{n+1}$), and adjusting the maximum frequency according to the measured intracardiac bio-impedance. The adjusting process can include evaluating a parameter representative of the cardiac flow ($d_n$, $d_{n+1}$) utilizing the intracardiac signal of bio-impedance; controlling a predetermined variation (X %) of the frequency (f) of delivery of the stimulation pulses; evaluating the correlative variation (y %) of the cardiac flow; and adjusting the value of the maximum frequency ($F_{max}$) according to the variation of the cardiac flow thus evaluated.

11 Claims, 3 Drawing Sheets

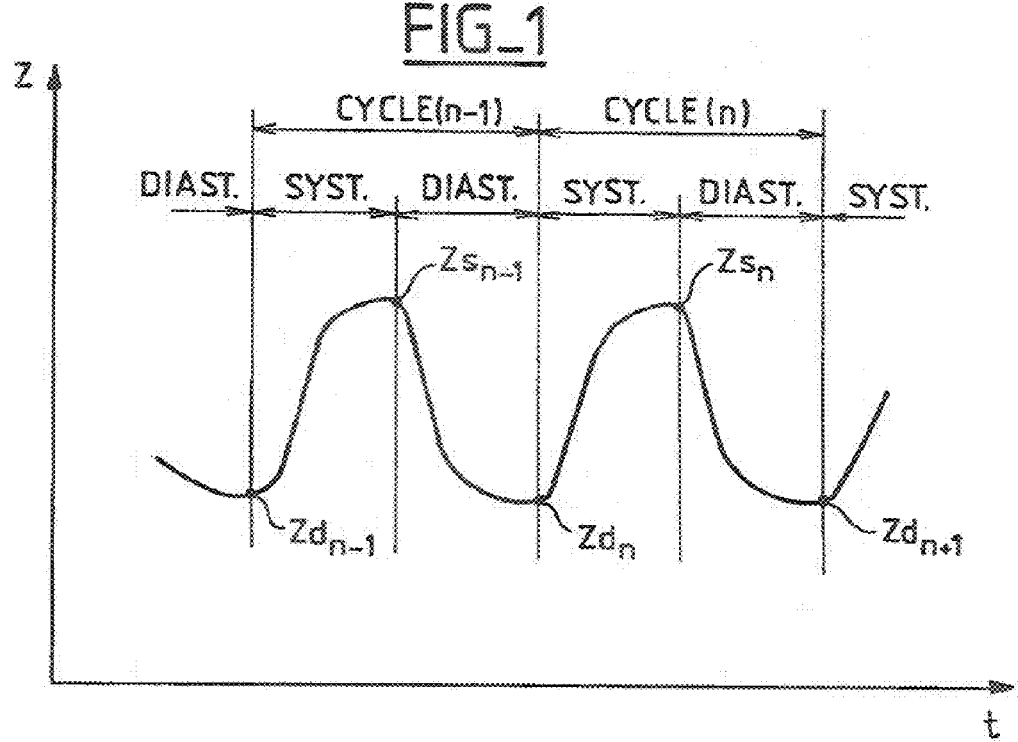
FIG_1
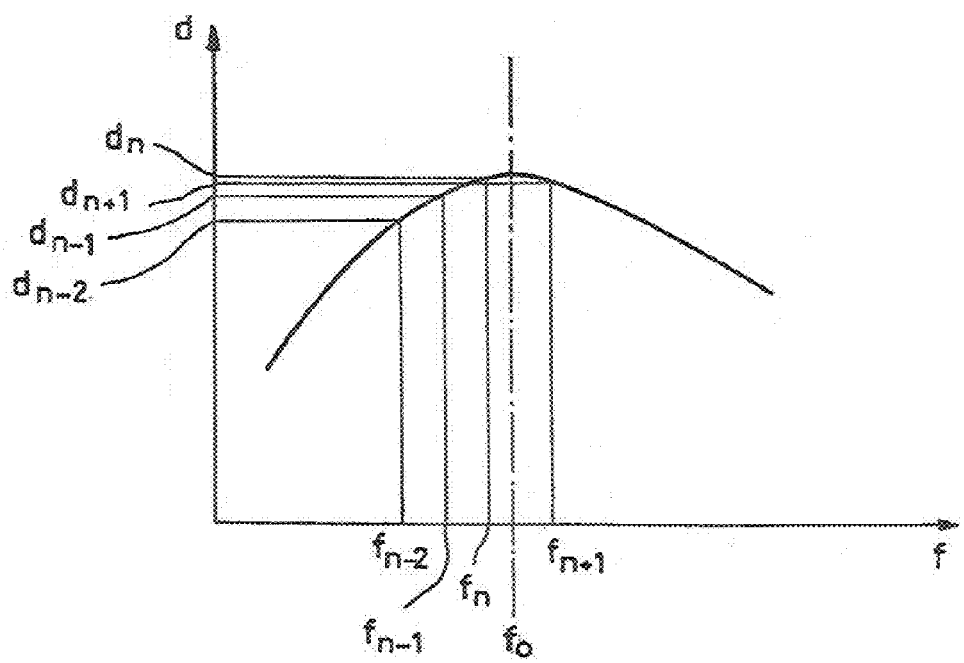
FIG_2

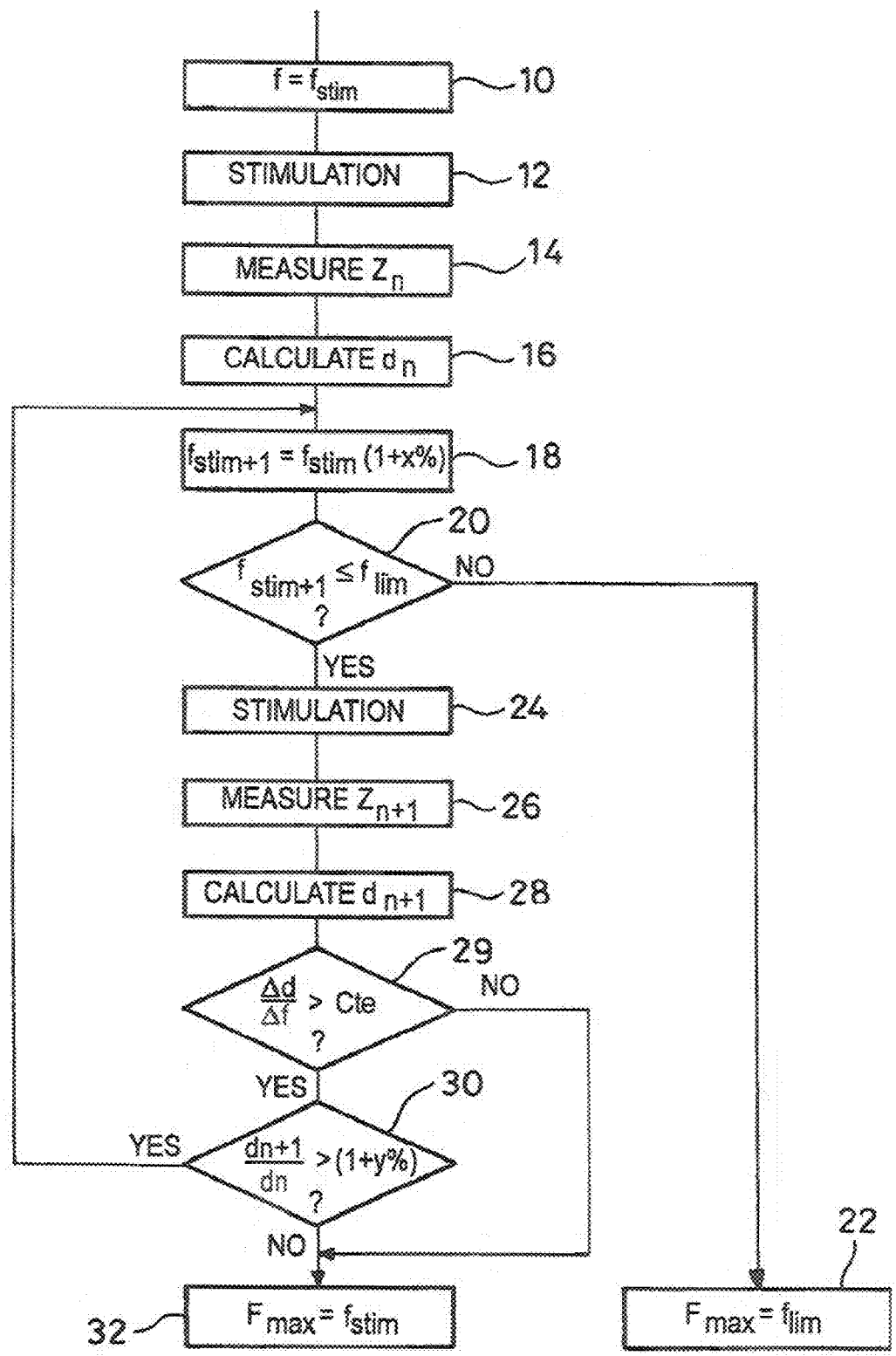

ADJUSTING THE MAXIMUM VENTRICULAR STIMULATION FREQUENCY ACCORDING TO THE HEMODYNAMIC STATE OF THE PATIENT IN AN ACTIVE IMPLANTABLE MEDICAL DEVICE

FIELD OF THE INVENTION

The present invention relates to "active implantable medical devices" as defined by the Jun. 20, 1990 directive 90/385/CEE of the Council of the European Communities, more particularly to cardiac devices such as pacemakers, defibrillators and/or cardiovertors that are able to deliver to the heart low energy stimulation pulses for the treatment of the disorders of the cardiac rate.

BACKGROUND OF THE INVENTION

In these devices, the ventricular stimulation frequency is variable, either by ensuring by the ventricle stimulation occurs in response to the atrial rate, or according to a parameter collected by a sensor. In the latter case, the known sensors are generally selected from among three types:

(1) A sensor of effort, which is a sensor measuring a parameter that is preponderantly physiological, and generally the measurement of the minute-ventilation, denominated a "sensor MV", or the oxygen saturation in blood, or the temperature, etc. Such a sensor provides an adequate representation of the metabolic needs of the patient, according to whether the patient is at rest, in exercise, in recovery after effort, etc.

(2) A sensor of activity which is generally an accelerometer integrated into the pacemaker, denominated by the common name of "sensor G", intended to quickly detect a change of the posture or of the dynamic of the patient carrying the apparatus, in particular to detect the beginnings of a phase of effort revealed by a significant increase in the patient's physical movements.

(3) A hemodynamic sensor: it is a question in this case of operating a control algorithm based upon a signal representative of the blood flow.

The effort sensor, also called a physiological sensor, delivers a signal that is well correlated to the real metabolic needs of the patient, but with a response time that is relatively long, and with a low sensitivity to low levels of effort.

Activity sensors on the other hand are sensors with a very short response time, but which measure a purely mechanical parameter (acceleration) that is non-physiological in nature, and therefore lacks specificity. Such a sensor does not allow, for example, to distinguish between a real beginning of an effort from vibrations or movements undergone in a purely passive way, for example traveling in a car, in which latter case the patient is not exerting any particular effort.

Rate responsive pacemakers are known that use one of these types of sensors to adjust permanently various parameters such as the stimulation frequency, the atrio-ventricular delay (AVD), or the inter-ventricular delay in the case of a bi-ventricular stimulation. There are also pacemakers combining two (or more) types of sensors, so as to avoid the disadvantages associated with each one.

The algorithms for controlling pacemakers in addition envisage a parameter known as the "maximum frequency" or "Fmax", which is the maximum frequency of ventricular stimulation. This parameter is applicable in particular when it is a question of ensuring the follow-up of the atrial rate by the ventricle: Fmax is then the higher limit to which the pacemaker can synchronize a ventricular stimulation on each atrial detection in the conventional DDD pacing mode. This Fmax parameter is in particular used to set a maximum limit for the stimulation frequency that may be calculated by algorithms such as the smoothing functions of rate response functions. In a rate responsive pacemaker, Fmax is used to make the dynamics of the sensor correspond to the upper limit value that the stimulation frequency can take.

In a double-chamber pacemaker, the maximum frequency also is used as a reference value, in comparison with the detected atrial frequency in order to limit the ventricular stimulation frequency when the atrial rate exceeds Fmax, for example, by applying an operating mode known as the "Wenckebach mode".

The maximum frequency is generally programmed once at a value determined by the physician, mainly according to the age of the patient, with a possible weighting factor due to the capacity of effort of the patient and/or the presence of a cardiopathy or a cardiomyopathy.

It has been proposed to vary the maximum frequency in a way controlled over the course of time, as, for example, described in EP-A-1 059 099 and its corresponding Published U.S. Application 2000US-09589339 000607 (commonly assigned herewith to Ela Médical), where this frequency is automatically and gradually recorded over the course of time according to the hemodynamic improvement of the state of the patient.

A mechanism for the adjustment of the maximum frequency was also proposed by U.S. Pat. No. 6,119,040 (Chirife), which describes a pacemaker of the type controlled by an activity sensor (an accelerometer or similar component) included in the case of the pacemaker. To compensate for the fact that such a control sensor is not correlated with the metabolic needs for the patient, this document proposes to make variable the maximum frequency by adjusting the latter in an automatic way according to a physiological parameter. Thus, a significant increase of the stimulation frequency in response to a situation of activity detected by an accelerometer is allowed only if there is confirmation of a significant increase in the metabolic requirements. This makes it possible to make a little more specific the rate responsive function of the pacemaker, while adding to it a significant safety parameter. In this document, the physiological parameter used to regulate the maximum frequency is the ventricular pre-ejection period (PEP), namely the interval of time included between the detection of a beginning of cardiac cycle (spontaneous or stimulated) and the beginning of the ventricular ejection: during this interval of time, the ventricle contracts but its volume does not change (isovolumic contraction), only the pressure inside the ventricle increases. The PEP ends as soon as the aortic valve and the pulmonary valve open, which has as a consequence the ejection of blood in the arteries, with a correlative reduction of the volume of the ventricles, which continues until the end of the diastole.

According to this document, the PEP is evaluated utilizing an intracardiac measurement of bio-impedance: this parameter indeed gives a dynamic image of the contraction of the myocardium. The analysis of the variations of impedance makes it possible to characterize the evolution of the systolic and diastolic phases, and thus the duration of the PEP. An increase in the cardiac rate that would not be associated with a corresponding shortening of the PEP is regarded as inadequate or excessive compared to the physiological needs for the patient. This makes it possible to compensate or, at the very least, to limit the effects of the non-physiological character of the activity sensor used for the control of the pacemaker.

It has been appreciated by the present inventor that if one fixes the maximum frequency at a given value, pre-programmed, this adjustment does not take into account the general hemodynamic state of the patient, and even less his evolution over the course of time, for example, in the case of an improvement or, on the contrary, in the case of an aggravation, of this state. Indeed, if the heart rate is too high, the heart will not properly fill with blood in a satisfactory manner, and consequently the volume of ejection falls. It is thus the case in such situations of tachycardia or fibrillation, and also in the case of application of stimulation pulses at too high a frequency, due to a bad adjustment of the maximum frequency compared to the actual state of the patient.

There is thus a turning point frequency at which the benefit obtained by an increase in blood flow from an increase in the stimulation frequency is lost by the reduction in the volume of ejection. It is thus important not to exceed this turning point frequency, under a penalty of a reduction in the cardiac flow.

OBJECTS AND SUMMARY OF THE INVENTION

It is therefore an object of the present invention to propose an adaptive mechanism for the maximum frequency.

Broadly, the present invention concerns adapting the maximum frequency so that the stimulation frequency does not exceed a point where the flow/frequency characteristic becomes decreasing, by readjusting if necessary the maximum frequency to take account of the evolution of the flow/frequency characteristic, which characteristic in turn depends on the general hemodynamic state of the patient. More particularly, the flow is evaluated by an intracardiac measurement of bio-impedance, typically one of a trans-valvular, a trans-septum or an intraventricular impedance, each measurement technique being well known in the art.

As the inventor has appreciated, under strict conditions of time, given the heartbeat rate and the state of the sensor employed in the device, daily variations of the average hemodynamic parameters that will be obtained by an intracardiac measurement of bio-impedance are representative of the evolution of the state of the heart of the patient. A typical hemodynamic parameter useful in this regard is the cardiac flow, or a parameter that is closely correlated to it, such as the fraction of ejection. More specifically, the measurement of the right trans-valvular bio-impedance is representative of the evolution of the right heart, while the measurement of the trans-septum bio-impedance is representative of the evolution of the left and right hearts.

These variations also reflect, in an indirect manner, what occurs on the lungs, on the left heart and on the oxygenated tissues of the patient, because of the general repercussion in the organism of the blood flow in the right heart. Thus, in the case of a double-chamber pacemaker, if the evolution of the average index reveals a hemodynamic deterioration of the state of the patient but the cardiac activity remains satisfactory, then the physician will be able to suspect a pulmonary insufficiency.

For this purpose, the present invention is broadly directed to an active implantable medical device of the general type described in U.S. Pat. No. 6,119,040 mentioned above, i.e., including: means for delivering stimulation pulses on at least one site of a cardiac cavity; means for controlling the rate of delivery of the stimulation pulses; means for limiting to a maximum frequency the rate of delivery of the stimulation pulses; means for measuring an intracardiac bio-impedance; and means for adjusting the maximum frequency to modify the value of the maximum frequency according to the measured intracardiac bio-impedance. U.S. Pat. No. 6,119,040 is incorporated herein by reference in its entirety.

According to the invention, the maximum frequency adjusting means includes: means for evaluating a parameter representative of the cardiac flow based upon a signal delivered by the means for measuring the intracardiac bio-impedance; means for controlling a predetermined variation of the frequency of delivery of the stimulation pulses; means for evaluating a correlative variation of the cardiac flow; and means for adjusting the value of the maximum frequency according to the variation of the cardiac flow thus evaluated.

The means for adjusting the maximum frequency are more preferably means operating in an iterative way, able to control successive predetermined variations of the stimulation frequency, and to evaluate with each iteration the correlative variation of the cardiac flow.

The maximum frequency adjusting means preferable terminates the iterative operation when, for successive increments of the stimulation frequency, the correlative variation of the cardiac flow falls below a given threshold, the threshold being, for example, a given percentage of an increase in the cardiac flow, in relation with a given percentage of increase in the stimulation frequency. The adjusting means then adjusts the value of the maximum frequency to the value of the stimulation frequency which had been applied to the penultimate iteration. The threshold can be a fixed threshold as noted, in particular a given percentage of increase in the cardiac flow, in relation to a given percentage of increase in the stimulation frequency, or a variable threshold, adjusted dynamically according to the heart rate or the cardiac flow.

Advantageously, the adjusting means also can cease iterative operation if the incrementing of the stimulation frequency increases the stimulation frequency above a predetermined limit value.

The means for evaluating the parameter representative of the cardiac flow can be means operating on values of peaks of diastolic impedance and systolic impedance that are determined by the means for measuring intracardiac bio-impedance, or operating by an integration of the intracardiac bio-impedance measurement signal, this integration being operated between successive peaks of diastolic impedance and/or systolic impedance.

The physiological sensor is preferably a minute-ventilation sensor operating by a measurement of trans-pulmonary bio-impedance.

The maximum frequency adjusting means can, after having adjusted the value of the maximum frequency, adjust an atrio-ventricular delay value and/or an inter-ventricular delay value. In this case, they advantageously include, as previously, means for controlling a predetermined variation of the atrio-ventricular delay and/or inter-ventricular delay, means for evaluating the correlative variation of the cardiac flow, and means for adjusting the value of the atrio-ventricular delay and/or inter-ventricular delay according to the variation of the cardiac flow thus evaluated. These means can in particular operate in an iterative way, by controlling successive predetermined variations of the atrio-ventricular delay and/or inter-ventricular delay, and by evaluating with each iteration the correlative variation of the cardiac flow.

BRIEF DESCRIPTION OF THE DRAWING

Further benefits, features and characteristics of the present invention will become apparent to a person of ordinary skill in the art in view of the following detailed description of a preferred embodiment of the invention, made with reference to the annexed drawings, in which like reference characters refer to like elements, and in which:

FIG. 1 is a diagram showing the evolution of the intracardiac impedance as a function of time during two successive cardiac cycles;

FIG. 2 illustrates the characteristic giving the cardiac flow according to the stimulation frequency;

FIG. 3 is a flow chart illustrating the way in which the maximum frequency is, according to the invention, adjusted close to the maximum of the characteristic of FIG. 2.

DETAILED DESCRIPTION OF THE INVENTION

Figure 4:
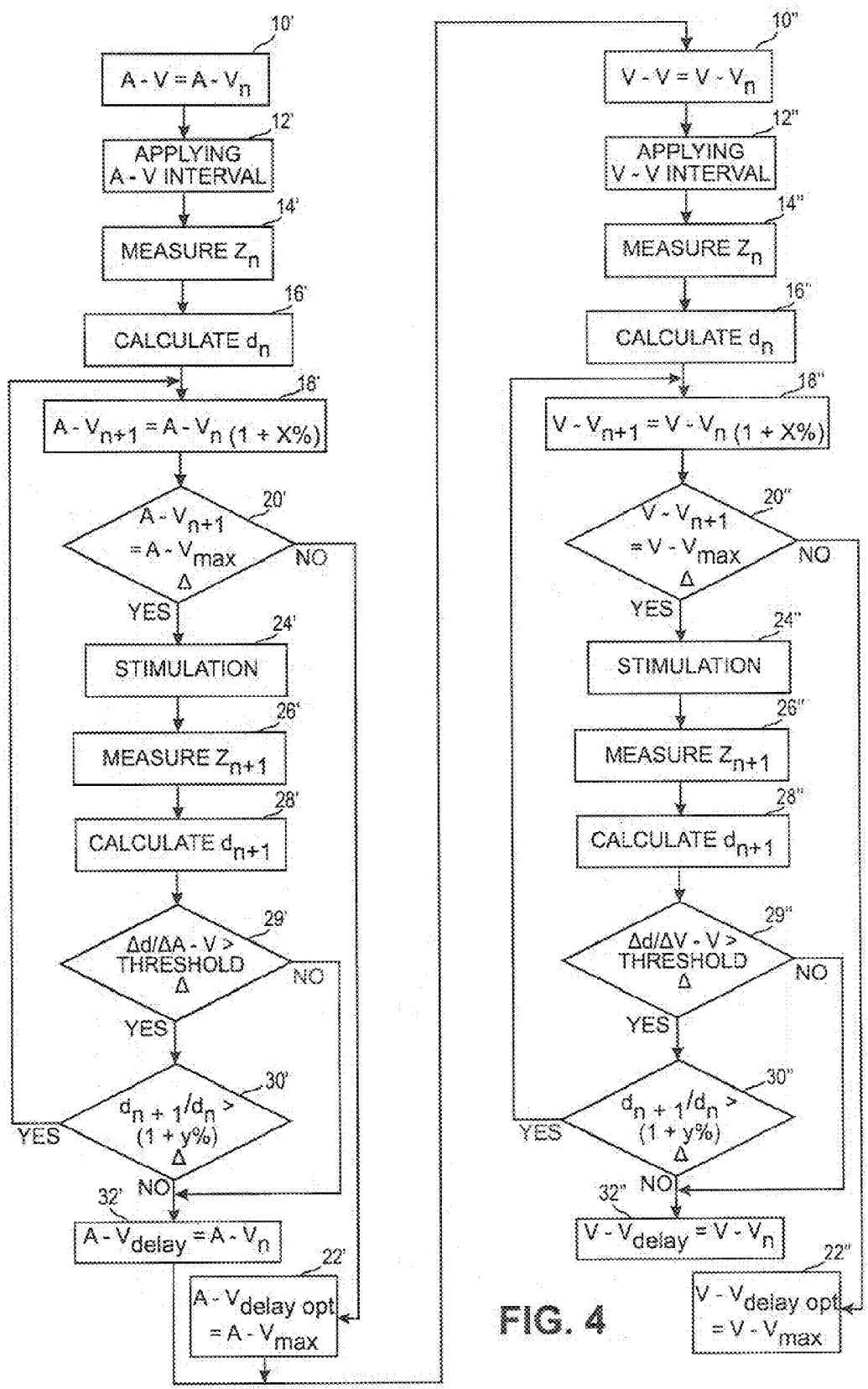
FIG. 4 is a flow chart illustrating the way in which the A-V delay and V-V delay are, according to the invention, adjusted close to the maximum of the characteristic in FIG. 2.

The present invention concerns, in a general way, a cardiac pacemaker (or a defibrillator, cardiovertor or multisite device), more preferably a rate responsive device enslaved to an effort sensor (physiological sensor), typically a minute-ventilation sensor. The minute-ventilation is a factor representative of the instantaneous metabolic needs of the patient, and it is evaluated by a measurement of trans-pulmonary bio-impedance, i.e., operated (or measured) between the heart and the case of the pacemaker, located in the top of the thorax, as is well known in the art.

The invention primarily proposes to modify the stimulation frequency maximum (hereafter Fmax) according to an improvement or no improvement of the cardiac flow in the patient carrying the device, this flow being evaluated by an intracardiac measurement of bio-impedance.

The measurement of an intracardiac bio-impedance is a technique in itself known. EP-A-1 116 497 and its counterpart U.S. Pat. No. 6,604,002, commonly assigned herewith to Ela Medical describe making a dynamic measurement of intracardiac bio-impedance to evaluate diastolic and systolic volumes, and to thus obtain an indication of the cardiac flow, and thus in turn an indication of the fraction of ejection. The signal obtained is used to control the heart rate and/or the atrio-ventricular delay in the direction of the maximization of the flow; it is also proposed to use this parameter to control the inter-ventricular delay in the case of a bi-ventricular stimulation.

More particularly, U.S. Pat. No. 6,604,002 also describes is a technique for measurement of the trans-valvular bio-impedance (between the atrium and the ventricle located on the same side of the heart) by a tripolar configuration, with injection of a current pulse between an atrial site and a ventricular site, and collection of a differential potential between an atrial site and a ventricular site, with one of the sites common to the injection and the collection, a specific site for the injection and a specific site for the collection. The current injected is current of low amplitude, insufficient to excite the cardiac cells. U.S. Pat. No. 6,604,002 is incorporated by reference herein in its entirety.

EP-A-1 138 346 and its counterpart U.S. Pat. No. 6,725,091, also assigned to ELA Médical describes another type of bio-impedance measurement, that of a trans-septum bio-impedance, i.e., between one site located on one side of the heart and a site located on other side of the heart, with an oblique trans-septum configuration (between a ventricle and an atrium located on the opposite side) or inter-ventricular trans-septal configuration (between the two ventricles). This technique allows one to obtain a value representative of the fraction of ejection, although the signal is lower than in the case of the measurement of a trans-valvular bio-impedance, and is also influenced by the self-impedance of the tissues of the septum. In addition, while the trans-valvular bio-impedance is correlated with the flow in the right heart, the trans-septum bio-impedance, oblique or inter-ventricular, is correlated with the flow in the left heart. U.S. Pat. No. 6,725,091 is incorporated by reference herein in its entirety.

With respect to FIG. 1, the variation of intracardiac impedance Z is illustrated, more particularly of a trans-valvular impedance, during two successive cardiac cycles. In a general way, for the purposes of the present invention, measurements of intracardiac bio-impedance can be done by any of a bipolar, tripolar or quadripolar measurement configuration (or more than 4 poles), according to techniques in themselves known to persons of ordinary skill in the art which will not be described here in detail.

The values of impedance $Zd_{n-1}$, $Zs_{n-1}$, $Zd_n$, $Zs_n$, $Zd_{n+1}$, etc. which correspond to the beginnings of the successive systolic and diastolic phases are detected by the change of the direction of variation of the curve of impedance Z. The difference between the systolic impedance Zs and the diastolic impedance Zd gives a value correlated to the volume of ejection; the relationship between the volume and the intracardiac impedance not being necessarily linear, a compensation may be necessary.

Other techniques are possible to evaluate the volume of ejection, for example, by determining the integral of the curve between the each of the following two values:

1) the initial diastolic impedance $Zd_n$ and the systolic impedance $Zs_n$ of the same cycle (cycle n), 2) the systolic impedance $Zs_n$ and the final diastolic impedance $Zd_{n+1}$ of the same cycle (cycle n), 3) the systolic impedances $Zs_{n-1}$ and $Zs_n$ of two successive cycles, or 4) the diastolic impedances $Zd_{n-1}$ and $Zd_n$ of two successive cycles.

The volume of ejection thus determined can eventually be averaged over a programmed number of cardiac cycles.

Utilizing the eventually averaged value of the volume of ejection, it is possible to determine the cardiac flow:

flow (in 1/min)=volume of ejection (in $L$)×heart rate (in bpm)

The invention proposes, by using the measurements of cardiac flow thus obtained, to vary the stimulation frequency F so as to approach more closely the peak of the flow/frequency characteristic, illustrated in FIG. 2, and to give to the maximum frequency Fmax the value of the frequency $f_0$ corresponding to this maximum, or the nearest possible value to the latter.

The corresponding mechanism is an iterative mechanism, proceeding by successive approximations, illustrated on the flow chart of FIG. 3. For a given stimulation frequency (stage 10), the device produces a stimulation (stage 12) and measures the corresponding variations of intracardiac impedance (stage 14). As indicated above, the corresponding flow $d_n$ is then evaluated (stage 16).

The device increases then the stimulation frequency by a certain quantity, for example, by X % (stage 18). In the alternative, instead of a proportional increase, one could increase the stimulation frequency by constant steps.

The algorithm then checks (stage 20) that the stimulation frequency thus increased does not exceed a limit value $f_{lim}$, previously fixed by the physician at the time of the programming of the device as an unconditional limit. Indeed, as the maximum frequency $F_{max}$ is recomputed with regular intervals instead of being a fixed parameter, it is significant that it cannot reach values which, in any event, would be regarded as excessive and dangerous for the patient. If this limit frequency $f_{lim}$ is reached or exceeded, the automatic operation of the algorithm is terminated and one gives to Fmax the value of the frequency limit $f_{lim}$ (stage 22). The algorithm remains terminated (i.e., non-operational) until a restore event occurs. The restore event may be one or more of the following: (1) The patient returns to an effort state as detected by a sensor (e.g., a sensor MV or sensor G), (2) when the atrial rate increases by some predetermined percentage (e.g., when there is no sensor) and (3) after a programmable time delay, e.g., 3.0 hours, in the absence of a detected change in cardiac frequency.

In the contrary case, the device produces a stimulation with the frequency plus X % (stage 24), measures the new corresponding intracardiac impedance (stage 26), and evaluates the new value of the flow (stage 28).

In stage 29, the device checks that the rate of increase $\Delta d/\Delta f$ is positive, i.e. one is on an increasing part of the curve: if $\Delta d/\Delta f$ is positive, one moves towards a maximum. On the other hand, if $\Delta d/\Delta f$ is a null, one is at the maximum and if $\Delta d/\Delta f$ is negative this maximum is exceeded; to preserve a margin of error, one fixes as a criterion $\Delta d/\Delta f >$ a constant threshold. Then (stage 30) the algorithm determines if, for the increase by X % of the frequency, the cardiac flow increased at least by y % (X and y being programmable values defined in advance).

In the affirmative case, this means that the frequency/flow couple is placed on a point of the characteristic of FIG. 2 being on the increasing part of this characteristic, with a slope still relatively significant, and that this point is thus still rather far away from the maximum (such is the case of the frequencies $f_{n-2}$ and $f_{n-1}$ on FIG. 2).

In the contrary case, i.e., if the cardiac flow increases by y % less when the frequency of simulation increased by X %, it is considered that the frequency $f_0$ corresponding to the maximum of the characteristic was exceeded, or that one is located in a range very close to this maximum (case of the frequencies $f_n$ and $f_{n+1}$ of FIG. 2).

The iteration is then terminated, and the maximum frequency Fmax is fixed at the value of the penultimate stimulation frequency, i.e., the frequency that had been applied before the last increase in X % (stage 32).

Of course, as indicated above, at each iteration one checks that the stimulation frequency does not exceed the limit frequency $F_{lim}$ fixed in advance, even if the maximum of the characteristic is not reached.

In addition, it should be understood that the invention can be applied to the controlling of a parameter other than the maximum frequency, in particular an A-V delay (atrio-ventricular delay), or V-V delay (inter-ventricular delay, in the case of a bi-ventricular stimulation).

All that has just been described above in connection with the adjustment of the maximum frequency of ventricular stimulation $F_{max}$ can thus be directly transposed, mutatis-mutandis, to the adjustment of an A-V delay or a V-V delay (in alternative, as well as in addition to the adjustment of Fmax), as shown in FIG. 4. FIG. 4 is a flow chart that illustrates the adjustment of $F_{max}$ transposed to the adjustment of an A-V delay and V-V delay, wherein the labeled prime and double-prime steps of FIG. 4 correspond to the unprimed numbered steps of FIG. 3, but for the replacement of the frequency value with the A-V or V-V values where necessary.

Thus, to control the V-V delay in the direction of a maximization of the flow, the device must permanently seek the optimum of the stimulation frequency, of the V-V delay, and of the A-V delay. To do this, the maximum frequency $F_{max}$ is initially optimized, then the A-V delay is optimized as shown in steps 10', 12', 14', 16', 18', 20', 22', 24', 26', 28', 29', 30', and 32', by seeking an optimum by successive approaches, following the technique described above. Finally the optimum of V-V delay is sought as shown in steps 10", 12", 14", 16", 18", 20", 22", 24", 26", 28", 29", 30", and 32" (the order of these operations can be modified). The research of the optimum is done while decreasing or increasing the value in order to determine the optimal direction of variation, then by refining the value; each time the frequency, or the flow, changes, a new optimization routine is launched or at programmed time intervals (hours, days, etc.).

Suitable devices for which the present invention has application include, for example, the active implantable medical devices available from Ela Médical, Montrouge France. These devices are microprocessor based systems having circuits for receiving, conditioning and processing detected electrical signals, and are capable of receiving software instructions by telemetry, storing them in memory, and then executing those instructions to perform the functions described above in implementing the present invention. The creation of suitable software instructions for controlling an implant to perform the aforementioned functions of the present invention are believed to be within the abilities of a person of ordinary skill in the art. The detection circuits used to detect the cardiac signals in the atrium and the ventricular, in the left and/or right chambers, and the current injection circuits for measuring bio-impedance characteristics, are well known and any suitable design may be used.

One skilled in the art will appreciate that the present invention can be practiced by other than the described embodiments, which are presented for purposes of illustration and not of limitation.

I claim:

1. An active implantable medical device, comprising means for delivering stimulation pulses to at least one site of a cardiac cavity;

means for controlling a delivery frequency of the stimulation pulses;

means for limiting to a maximum frequency the delivery frequency of the stimulation pulses;

means for measuring an intracardiac bio-impedance;

means for adjusting the maximum frequency to a value that is a function of the measured intracardiac bio-impedance;

means for evaluating a parameter representative of cardiac flow based upon a signal delivered by the means for measuring the intracardiac bio-impedance;

means for changing the delivery frequency of the stimulation pulses in a successive cardiac cycle by a programmable variation (X %);

means for measuring a change in the parameter representative of cardiac flow over the successive cardiac cycle;

means for evaluating a first condition, the first condition being that the ratio of the change in the parameter representative of cardiac flow with respect to the change of the delivery frequency of the stimulation pulses over the successive cardiac cycle is greater than a threshold;

means for evaluating a second condition if the first condition is met, the second condition being that the change of the parameter representative of cardiac flow is greater than a programmable variation (y %), wherein the means for adjusting the maximum frequency adjusts the maximum frequency when the second condition is not met; and means for operating the means for adjusting the maximum frequency if the second condition is met in an iterative operation to control successive programmable variations of the delivery frequency of the stimulation pulses in response to the change in the parameter representative of cardiac flow with each iteration.

2. The active implantable medical device of claim 1, wherein the means for adjusting the maximum frequency further comprises means for terminating said iterative operation if the second condition is not met.

3. The active implantable medical device of claim 2, wherein said threshold is a fixed threshold.

4. The active implantable medical device of claim 2, wherein the means for adjusting the maximum frequency adjusts to the value of the delivery frequency of the stimulation pulses that had been applied to a penultimate iteration in response to the termination of the iteration operation.

5. The active implantable medical device of claim 1, wherein the means for adjusting the maximum frequency further comprises means for terminating the iteration operation in response to an increase of the delivery frequency of the stimulation pulses above a predetermined limit value.

6. The active implantable medical device of claim 1, wherein the means for measuring an intracardiac bio-impedance further comprises means for measuring a peak diastolic impedance and means for measuring a peak systolic impedance, and wherein the means for evaluating a parameter representative of cardiac flow utilizes the peak diastolic impedance and the peak systolic impedance.

7. The active implantable medical device of claim 1, wherein the means for measuring an intracardiac bio-impedance further comprises means for measuring a peak diastolic impedance and means for measuring a peak systolic impedance and wherein the means for evaluating a parameter representative of cardiac flow further comprises means for calculating the integrals of the measured intracardiac bio-impedance successive peaks of at least one of the group consisting of the peak diastolic impedance and the peak systolic impedance.

8. The active implantable medical device of claim 1, wherein said means for adjusting the maximum frequency further comprises means, after having adjusted the value of the maximum frequency, for adjusting at least one of the group consisting of a value of the atrio-ventricular delay and a value of the inter-ventricular delay.

9. The active implantable medical device of claim 8, wherein the means for adjusting the maximum frequency further comprises means for controlling a programmable variation of at least one of the group consisting of the atrio-ventricular delay and the inter-ventricular delay, means for evaluating the correlative variation of the cardiac flow, and means for adjusting at least one of the group consisting of the value of the atrio-ventricular delay and inter-ventricular delay according to the evaluated variation of the cardiac flow.

10. The active implantable medical device of claim 8, wherein the means for adjusting the frequency maximum further comprises means operating in an iterative way, to control successive programmable variations of at least one of the group consisting of the atrio-ventricular delay and inter-ventricular delay, and to evaluate with each iteration the correlative variation of the cardiac flow.

11. An active implantable medical device, having computer readable instructions stored in memory for performing the steps of:
  delivering stimulation pulses to at least one site of a cardiac cavity;
  controlling a delivery frequency of the stimulation pulses;
  limiting to a maximum frequency the delivery frequency of the stimulation pulses;
  measuring an intracardiac bio-impedance;
  adjusting the maximum frequency to a value that is a function of the measured intracardiac bio-impedance;
  evaluating a parameter representative of cardiac flow based upon a signal delivered by the means for measuring the intracardiac bio-impedance;
  changing the delivery frequency of the stimulation pulses in a successive cardiac cycles, causing a change of the delivery frequency of the stimulation pulses by a programmable variation (X %);
  measuring a change in the parameter representative of cardiac flow over the successive cardiac cycle;
  evaluating a first condition, the first condition being that the ratio of the change in the parameter representative of cardiac flow with respect to the change of the delivery frequency of the stimulation pulses over the successive cardiac cycle is greater than a threshold;
  evaluating a second condition if the first condition is met, the second condition being that the change of the parameter representative of cardiac flow is greater than a programmable variation (y %), wherein the maximum frequency is adjusted when the second condition is not met; and
  adjusting the maximum frequency if the second condition is met in an iterative operation to control successive programmable variations of the delivery frequency of the stimulation pulses in response to the change in the parameter representative of cardiac flow with each iteration.

* * * * *